(12) United States Patent
Maase et al.

(10) Patent No.: US 7,605,297 B2
(45) Date of Patent: Oct. 20, 2009

(54) METHOD FOR EXTRACTING IMPURITIES USING IONIC LIQUIDS

(75) Inventors: Matthias Maase, Speyer (DE); Manuel Budich, Böhl-Iggelheim (DE); Georg Großmann, Mannheim (DE); Laszlo Szarvas, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 546 days.

(21) Appl. No.: 10/565,187

(22) PCT Filed: Jul. 3, 2004

(86) PCT No.: PCT/EP2004/007254

§ 371 (c)(1),
(2), (4) Date: Oct. 12, 2006

(87) PCT Pub. No.: WO2005/019137

PCT Pub. Date: Mar. 3, 2005

(65) Prior Publication Data

US 2007/0193952 A1   Aug. 23, 2007

(30) Foreign Application Priority Data

Jul. 21, 2003   (DE) ............................... 103 33 258

(51) Int. Cl.
*A62D 3/36*   (2007.01)
(52) U.S. Cl. ...................... 588/318; 588/405
(58) Field of Classification Search ............... 588/405, 588/406
See application file for complete search history.

(56) References Cited

U.S. PATENT DOCUMENTS

| 2003/0091489 A1* | 5/2003 | Hommeltoft ............... 423/210 |
| 2003/0199723 A1* | 10/2003 | Hommeltoft ............... 585/856 |
| 2005/0010076 A1 | 1/2005 | Wasserscheid et al. |

FOREIGN PATENT DOCUMENTS

| DE | 101 55 281 | 6/2003 |
| EP | 1 310 543 A | 5/2003 |
| EP | 1 354 863 A | 10/2003 |
| WO | WO-01/40150 | 6/2001 |
| WO | WO-02/34863 A | 5/2002 |

OTHER PUBLICATIONS

Huddleston, J.G. et al., Chemical Communications—Chemcom, Royal Society of Chemistry, GB, 1998, pp. 1765-1766.
Visser et al., Green Chemistry, Feb. 2000, pp. 1-4.
Bekou et al., Oxford University Press, Sep. 2003.

* cited by examiner

*Primary Examiner*—Edward M Johnson
(74) *Attorney, Agent, or Firm*—Birch, Stewart, Kolasch & Birch, LLP

(57) ABSTRACT

The invention relates to a process for the extractive removal of phenols, alcohols, amines, phoshines, hydroxylamines, hydrazines, oximes, imines, water, carboxylic acids, amino acids, hydroxamic acids, sulfinic acids, sulfonic acids, peroxycarboxylic acids, phosphonous acids, phosphinous acids, phosphonic acids, phosphinic acids or phosphoric acids from aprotic solvents by means of ionic liquids of the formula $[K]_n{}^+[A]^{n-}$, where n, $[K]^+$ and $A^{n-}$ are defined as in the description.

20 Claims, No Drawings

METHOD FOR EXTRACTING IMPURITIES USING IONIC LIQUIDS

The present invention relates to a process for the extractive removal of phenols, alcohols, amines, phoshines, hydroxylamines, hydrazines, oximes, imines, water, carboxylic acids, amino acids, hydroxamic acids, sulfinic acids, sulfonic acids, peroxycarboxylic acids, phosphonous acids, phosphinous acids, phosphonic acids, phosphinic acids or phosphoric acids from aprotic solvents by means of ionic liquids of the formula $[K]_n^+[A]^{n-}$, where n is 1, 2 or 3;

[K]+ is selected from the group consisting of:

quaternary ammonium cations of the formula $[NR^1, R^2, R^3, R^4]^+$ (Ia), quaternary phosphonium cations of the formula $[PR^1, R^2, R^3, R^4]^+$ (Ib), where $R^1, R^2, R^3, R^4$ are each $C_1$-$C_{12}$-alkyl or phenyl-$C_1$-$C_4$-alkyl, where the aliphatic radicals may bear from 1 to 4 substitutents selected from the group consisting of halogen, amino, cyano, $C_1$-$C_4$-alkoxy and the phenyl ring may bear the above-mentioned substitutents and also $C_1$-$C_6$-alkyl, carboxylate and sulfonate groups;

$R^1$ and $R^2$ may together form a $C_4$-$C_5$-alkenylene radical which may be substituted by $C_1$-$C_4$-alkyl, halogen, cyano or $C_1$-$C_4$-alkoxy;

imidazolium cations of the formula,

(Ic)

pyridinium cations of the formula,

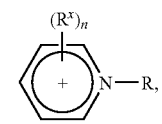
(Id)

pyrazolium cations of the formula,

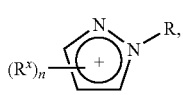
(Ie)

quinolinium cations of the formula,

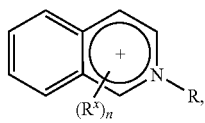
(If)

thiazolium cations of the formula,

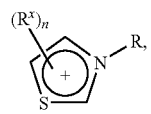
(Ig)

triazinium cations of the formula,

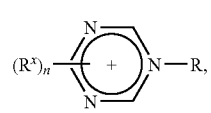
(Ih)

where the index n and the substitutents R and $R^x$ have the following meanings:

n is 0, 1, 2, 3 or 4;

R is hydrogen, $C_1$-$C_{12}$-alkyl or phenyl-$C_1$-$C_4$-alkyl, where the aliphatic radicals may bear from 1 to 4 substitutents selected from the group consisting of halogen, amino, cyano, $C_1$-$C_4$-alkoxy and the phenyl ring may bear the above-mentioned substitutents and also $C_1$-$C_6$-alkyl, carboxylate and sulfonate groups;

$R^x$ is $C_1$-$C_6$-alkyl, halogen, amino, cyano, $C_1$-$C_4$-alkoxy, carboxylate or sulfonate;

$[A]_n-$ is the partly or fully deprotonated anion of an inorganic or organic protic acid $H_nA$ (III), where n is a positive integer and indicates the charge on the anion.

Ionic liquids are a quite young area of research. In general, the term "ionic liquids" refers to salts which have a melting point below 100° C. Such a wide definition also comprises ionic liquids based on metal halides such as aluminum, zinc or copper chloride.

In the case of the present extracted process, ionic liquids based on metal halides, as are described, for example, in WO 01/40150, are not suitable since they would react with the protic, functional group of the molecule to be extracted.

For this reason, ionic liquids are defined more narrowly as above for the purposes of the present invention.

The extraction of sulfur impurities from fuels using the ionic liquids mentioned at the outset has been described in the literature (WO 01/40150, DE 101 55 281). The studies cited are based on the assumption that sulfur impurities are readily polarizable compounds while alkanes (fuels) are compounds which are not readily polarized.

It has now surprisingly been found that compounds bearing protic groups can also be extracted from hydrocarbons. The process not only gives good results in extractions from alkanes, but can astonishingly also be extended to extractions from aromatic hydrocarbons. The examples impressively demonstrate that cresol, which bears a (protic) OH group, can be efficiently extracted from the aromatic hydrocarbon chlorobenzene.

Ionic liquids can be prepared, for example, as described in the monograph by P. Wasserscheid and T. Welton "Ionic liquids in synthesis", Wiley-VCH 2003, by alkylation and/or ion exchange.

For the purposes of the present invention, ionic liquids are the salts defined at the outset. In the following, the ionic liquids are described in more detail, especially in terms of the nature of the anions.

Preferred cations are ammonium salts (1a) or 1,3-substituted imidazolium salts (Ic). Very particular preference is given to imidazolium salts (Ic) which comprise 1,3-dimethylimidazolium, 1-ethyl-3-methylimidazolium, 1-methyl-3-propylimidazolium, 1-isopropyl-3-methylimidazolium, 1-butyl-3-methylimidazolium, 1-methyl-3-pentyl-imidazolium, 1-hexyl-3-methylimidazolium, 1-heptyl-3-methylimidazolium, 1-methyl-3-octylimidazolium, 1-decyl-3-methylimidazolium, 1-methyl-3-benzylimidazolium, 1-methyl-3-(3-phenylpropyl)imidazolium, 1-(2-ethyl)hexyl-3-methylimidazolium, 1-methyl-3-nonylimidazolium, 1-methyl-3-decylimidazolium, 1,2,3-trimethylimidazolium, 1-ethyl-2,3-dimethylimidazolium or 1-butyl-2,3-dimethylimidazolium as 1,3-substituted imidazolium cation.

The ionic liquids used in the process of the present invention comprise an anion $A^{n-}$ which is the partly or fully deprotonated anion of an inorganic or organic protic acid $H_nA$ (III), where n is a positive integer and indicates the charge on the anion.

For the purposes of the present invention, a partly deprotonated anion is an anion of a polybasic acid which still comprises one or more deprotonatable hydrogen atoms. Correspondingly, a fully deprotonated anion is an anion which comprises no further deprotonatable hydrogen atoms.

Preferred anions $A^{n-}$ are:

fluoride; hexafluorophosphate; hexafluoroarsenate; hexafluoroantimonate; trifluoroarsenate; nitrite; nitrate; sulfate; hydrogensulfate; carbonate; hydrogen-carbonate; phosphate; hydrogenphosphate; dihydrogenphosphate, vinylphosphonate, dicyanamide, bis(pentafluoroethyl)phosphinate, tris(pentafluoroethyl)trifluorophosphate, tris(heptafluoropropyl)trifluorophosphate, bis[oxalato(2-)]borate, bis[salicylato(2-)]-borate, bis[1,2-benzenediolato(2-)-O,O'] borate, tetracyanoborate;

tetrasubstituted borate of the formula (IIa) $[BR^aR^bR^cR^d]^-$, where $R^a$ to $R^d$ are each, independently of one another, fluorine or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

organic sulfonate of the formula (IIb) $[R^e—SO_3]^-$, where $R^e$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

carboxylate of the formula (IIc) $[R^f—COO]^-$, where $R^f$ is hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

(Fluoroalkyl)fluorophosphate of the formula (IId) $[PF_x(C_yF_{2y+1-z}H_z)_{6-x}]^-$, where $1 \leq x \leq 6$, $1 \leq y \leq 8$ and $0 \leq z \leq 2y+1$;

imide of the formula (IIe) $[R^g—SO_2—N—SO_2—R^h]^-$, (IIf) $[R^i—SO_2—N—CO—R^j]^-$ or (IIg) $[R^k—CO—N—CO—R^l]^-$, where $R^g$ to $R^l$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

methide of the formula (IIh)

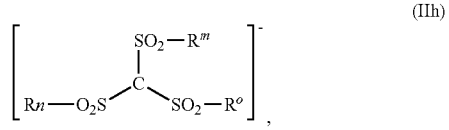

where $R^m$ to $R^o$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

organic sulfate of the formula (IIi) $[R^pO—SO_3]^-$, where $R^p$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens.

The charge "n-" on the anion $A^{n-}$ is "1-", "2-" or "3-". Examples of doubly negatively charged anions are sulfate, hydrogenphosphate and carbonate. An example of a triply negatively charged anion is phosphate.

Possible heteroatoms are in principle all heteroatoms which are capable of formally replacing a —$CH_2$—, a —CH= group, a C≡ group or a =C= group. If the carbon-comprising radical comprises heteroatoms, preference is given to oxygen, nitrogen, sulfur, phosphorus and silicon. Preferred groups are, in particular, —O—, —S—, —SO—, —$SO_2$—, —NR—, —N=, —PR—, —$PR_2$ and —$SiR_2$—, where the radicals R are in each case the remaining part of the carbon-comprising radical.

Possible functional groups are in principle all functional groups which can be bound to a carbon atom or a heteroatom. Examples of suitable groups are —OH (hydroxyl), =O (in particular as a carbonyl group), —$NH_2$ (amino), =NH (imino), —COOH (carboxyl), —$CONH_2$ (carboxamide) and —CN (cyano). Functional groups and heteroatoms can also be directly adjacent, so that combinations of a plurality of adjacent atoms, for instance —O— (ether), —S— (thioether), —COO— (ester), —CONH— (secondary amide) or —CONR— (tertiary amide), are also comprised.

Preferred carbon-comprising organic, saturated or unsaturated, acyclic or cyclic, aliphatic, aromatic or araliphatic radicals having from 1 to 30 carbon atoms as the radicals $R^a$ to $R^d$ in tetrasubstituted borate (IIa), the radical $R^e$ in organic sulfonate (IIb), the radical $R^f$ in carboxylate (IIc) and the radicals $R^g$ to $R^l$ in the imides (IIe), (IIf) and (IIg) are, independently of one another, $C_1$-$C_{30}$-alkyl and their aryl-, heteroaryl-, cycloalkyl-, halogen-, hydroxy-, amino-, carboxy-, formyl-, —O—, —CO—, —CO—O— or —CO—N<-substituted derivatives, for example methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl(benzyl), diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl, methoxy, ethoxy, formyl, acetyl or $C_nF_{2(n-a)+(1-b)}H_{2a+b}$ where $n \leq 30$, $0 \leq a \leq n$ and $b=0$ or $1$ (for example $CF_3$, $C_2F_5$, $CH_2CH_2-C_{(n-2)}F_{2(n-2)+1}$, $C_6F_{13}$, $C_8F_{17}$, $C_{10}F_{21}$, $C_{12}F_{25}$);

$C_3$-$C_{12}$-cycloalkyl and their aryl-, heteroaryl-, cycloalkyl-, halogen-, hydroxy-, amino-, carboxy-, formyl-, —O—, —CO— or —CO—O-substituted derivatives, for example cyclopentyl, 2-methyl-1-cyclopentyl, 3-methyl-1-cyclopentyl, cyclohexyl, 2-methyl-1-cyclohexyl, 3-methyl-1-cyclohexyl, 4-methyl-1-cyclohexyl or $C_nF_{2(n-a)-(1-b)}H_{2a-b}$ where $n \leq 30$, $0 \leq a \leq n$ and $b=0$ or $1$;

$C_2$-$C_{30}$-alkenyl and their aryl-, heteroaryl-, cycloalkyl-, halogen-, hydroxy-, amino-, carboxy-, formyl-, —O—, —CO— or —CO—O-substituted derivatives, for example 2-propenyl, 3-butenyl, cis-2-butenyl, trans-2-butenyl or $C_nF_{2(n-a)-(1-b)}H_{2a-b}$ where $n \leq 30$, $0 \leq a \leq n$ and $b=0$ or $1$;

$C_3$-$C_{12}$-cycloalkenyl and their aryl-, heteroaryl-, cycloalkyl-, halogen-, hydroxy-, amino-, carboxy-, formyl-, —O—, —CO— or —CO—O-substituted derivatives, for example 3-cyclopentenyl, 2-cyclohexenyl, 3-cyclohexenyl, 2,5-cyclohexadienyl or $C_nF_{2(n-a)-3(1-b)}H_{2a-3b}$ where $n \leq 30$, $0 \leq a \leq n$ and $b=0$ or $1$; and aryl or heteroaryl having from 2 to 30 carbon atoms and their alkyl-, aryl-, heteroaryl-, cycloalkyl-, halogen-, hydroxy-, amino-, carboxy-, formyl-, —O—, —CO— or —CO—O-substituted derivatives, for example phenyl, 2-methylphenyl(2-tolyl), 3-methylphenyl(3-tolyl), 4-methylphenyl, 2-ethylphenyl, 3-ethylphenyl, 4-ethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 4-phenylphenyl, 1-naphthyl, 2-naphthyl, 1-pyrrolyl, 2-pyrrolyl, 3-pyrrolyl, 2-pyridinyl, 3-pyridinyl, 4-pyridinyl or $C_6F_{(5-a)}H_a$ where $0 \leq a \leq 5$.

If the anion $A^{n-}$ is a tetrasubstituted borate (IIa) $[BR^aR^bR^cR^d]^-$, preference is given to all four radicals $R^a$ to $R^d$ being identical and preferably being fluorine, trifluoromethyl, pentafluoroethyl, phenyl, 3,5-bis(trifluoromethyl)phenyl. Particularly preferred tetrasubstituted borates (IIa) are tetrafluoroborate, tetraphenylborate and tetra-[3,5-bis(trifluoromethyl)phenyl]borate.

If the anion $A^{n-}$ is an organic sulfonate (IIb) $[R^e-SO_3]^-$, the radical $R^e$ is preferably methyl, trifluormethyl, pentafluoroethyl, p-tolyl or $C_9F_{19}$. Particularly preferred organic sulfonates (IIb) are trifluoromethanesulfonate (triflate), methanesulfonate, p-toluenesulfonate, nonadecafluorononanesulfonate (nonaflate), dimethylene glycol monomethyl ether sulfate and octylsulfate.

If the anion $A^{n-}$ is a carboxylate (IIc) $[R^f-COO]^-$, the radical $R^f$ is preferably hydrogen, trifluoromethyl, pentafluoroethyl, phenyl, hydroxyphenylmethyl, trichloromethyl, dichloromethyl, chloromethyl, trifluoromethyl, difluoromethyl, fluoromethyl, ethenyl (vinyl), 2-propenyl, —CH═CH—COO⁻, cis-8-heptadecenyl, —CH₂—C(OH)(COOH)—CH₂—COO⁻ or unbranched or branched $C_1$-$C_{18}$-alkyl, for example methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, heptadecyl. Particularly preferred carboxylates (Vc) are formate, acetate, propionate, butyrate, valerate, benzoate, mandelate, trichloroacetate, dichloroacetate, chloroacetate, trifluoroacetate, difluoroacetate, fluoroacetate.

If the anion $A^{n-}$ is a (fluoroalkyl)fluorophosphate (IId) $[PF_x(C_yF_{2y+1-z}H_z)_{6-x}]^-$, z is preferably 0. Particular preference is given to (fluoroalkyl)fluorophosphates (IId), in which z=0, x=3 and $1 \leq y \leq 4$, specifically $[PF_3(CF_3)_3]^-$, $[PF_3(C_2F_5)_3]^-$, $[PF_3(C_3F_7)_3]^-$ and $[PF_3(C_4F_7)_3]^-$.

If the anion $A^{n-}$ is an imide (IIe) $[R^g-SO_2-N-SO_2-R^h]^-$, (IIf) $[R^i-SO_2-N-CO-R^j]^-$ or (IIg) $[R^kCO-N-CO-R^l]^-$, the radicals $R^g$ to $R^l$ are preferably each, independently of one another, trifluoromethyl, pentafluoroethyl, phenyl, trichloromethyl, dichloromethyl, chloromethyl, trifluoromethyl, difluoromethyl, fluoromethyl or unbranched or branched $C_1$-$C_{12}$-alkyl, for example methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl or dodecyl. Particularly preferred imides (IIe), (IIf) and (IIg) are $[F_3C-SO_2-N-SO_2-CF_3]^-$ (bis(trifluoromethylsulfonyl)imide), $[F_5C_2-SO_2-N-SO_2-C_2F_5]^-$ (bis(pentafluoroethylsulfonyl)imide), $[F_3C-SO_2-N-CO-CF_3]^-$, $[F_3C-CO-N-CO-CF_3]^-$ and those in which the radicals $R^g$ to $R^l$ are each, independently of one another, methyl, ethyl, propyl, butyl, phenyl, trichloromethyl, dichloromethyl, chloromethyl, trifluoromethyl, difluoromethyl or fluoromethyl.

If the anion $A^{n-}$ is a methide (IIh)

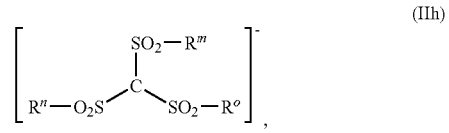

(IIh)

the radicals $R^m$ to $R^o$ are preferably each, independently of one another, trifluoromethyl, pentafluoroethyl, phenyl, trichloromethyl, dichloromethyl, chloromethyl, trifluoromethyl, difluoromethyl, fluoromethyl or unbranched or branched $C_1$-$C_{12}$-alkyl, for example methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl or dodecyl. Particularly preferred methides (IIh) are [(F$_3$C—SO$_2$)$_3$C]$^-$ (tris(trifluoromethylsulfonyl)methide), [(F$_5$C$_2$—SO$_2$)$_3$C]$^-$ (bis(pentafluoroethylsulfonyl)methide) and those in which the radicals R$^m$ to R$^o$ are each, independently of one another, methyl, ethyl, propyl, butyl, phenyl, trichloromethyl, dichloromethyl, chloromethyl, trifluoromethyl, difluoromethyl or fluoromethyl.

If the anion A$^{n-}$ is an organic sulfate (IIi) [R$^p$O—SO$_3$]$^-$, the radical R$^p$ is preferably a branched or unbranched C$_1$-C$_{30}$-alkylyl radical, particularly preferably methylsulfate, ethylsulfate, propylsulfate, butylsulfate, pentylsulfate, hexylsulfate, heptylsulfate or octylsulfate.

Very particularly preferred anions A$^{n-}$ are: tetrafluoroborate, hexafluorophosphate, trifluoromethanesulfonate, methanesulfonate, formate, acetate, mandelate, nitrate, nitrite, trifluoroacetate, sulfate, hydrogensulfate, methylsulfate, ethylsulfate, propylsulfate, butylsulfate, pentylsulfate, hexylsulfate, heptylsulfate, octylsulfate, phosphate, dihydrogenphosphate, hydrogenphosphate, propionate, bis(trifluoromethylsulfonyl)imide(triflimide), bis(pentafluoroethylsulfonyl)imide, tris(trifluoromethylsulfonyl)methide (methide), bis(pentafluoroethylsulfonyl)methide, p-toluenesulfonate (tosylate), bis[salicylato(2-)]borate, dimethylene glycol monomethyl ether sulfate, oleate, stearate, acrylate, methacrylate, maleate, hydrogencitrate, vinylphosphonate, bis(pentafluoroethyl)phosphinate, bis[oxalato(2-)]borate, bis[1,2-benzenediolato(2-)-O,O']borate, dicyanamide, tris(pentafluoroethyl)trifluoro-phosphate, tris(heptafluoropropyl)trifluorophosphate and tetracyanoborate.

For the purposes of the present invention, the organic compounds having protic, functional groups which are to be extracted are generally compounds or classes of compounds of the formula E-X—H, where E is hydrogen or optionally halogen-, C$_1$-C$_4$-alkoxy- or amino-substituted C$_1$-C$_{20}$-alkyl; optionally halogen-, alkyl- or methoxy-substituted phenyl, naphthyl or heteroaryl and X is —N(R')—, —O—, —P(R')—, —N(R')—O—, —N(R')—N(R'')—, —C(R')=N—O—, —C(=O)—O—, —S(=O)$_2$—O—, —S(=O)—O—, P(R')—, P(=O)(R')—, P(=O)(OR')—, P(=O)$_2$(R')—.

Specifically, the following organic compounds having protic, functional groups can be extracted using the process of the present invention:

alcohols such as C$_1$-C$_{20}$-alkanols, polyols, geminal diols (hydrates); silanols; amines such as aniline, N—C$_1$-C$_{20}$-alkylaniline, N—C$_1$-C$_{20}$-alkylamine, N,N-di-C$_1$-C$_{20}$-alkylamine; cyclic amines such as piperidine, piperazine, pyrrolidine, morpholine and ammonium salts; phosphines; amidines; hydrazines and hydrazinium salts, hydrazones; hydroxylamines and hydroxylammonium salts; carbamates; ureas; cyanohydrins; imines such as imidazole, aldimines (Schiff bases), ketimines and iminium salts; enamines such as pyrrole;

hydrazo compounds; hydroperoxides such as tert-butyl hydroperoxide; imides such as phthalimide; imino esters; oximes; hydrogen peroxide; water ("drying of solvents"); phenols such as hydroquinones, resorcinols, catechols, naphthol, binaphthol; phosphinous acids; phosphinic acids; phosphonic acids; monoalkyl (or aryl) phosphonates; phosphoric acid; monoalkyl (or aryl) phosphates; dialkyl (or aryl) phosphates; carboxylic acids; amino acids; hydroxycarboxylic acids; ketocarboxylic acids; hydroxamic acids; hydroxamosulfonic acids; sulfinic acids; sulfonic acids or peroxocarboxylic acids.

In particular, E-X—H is: unsubstituted or substituted phenol, for example o,m,p-cresol, 3-hydroxypyrazole, 2-hydroxypyridine, hydroquinone, resorcinol, catechol; C$_1$-C$_{20}$-alcohol, glycol, glycerol, optionally substituted aniline, for example N-C$_1$-C$_{20}$-alkylaniline, N—C$_1$-C$_{20}$-alkylamine, N,N-di-C$_1$-C$_{20}$-alkylamine, P—C$_1$-C$_{20}$-alkylphosphine, P,P-di-C$_1$-C$_{20}$-alkylphosphine, phenylphosphine, diphenylphosphine, hydrazine, hydroxylamine, sulfonic acid, sulfinic acid, phosphoric acid, carboxylic acid or amino acid.

E-X—H is particularly preferably: optionally substituted phenol, for example o,m,p-cresol, 3-hydroxypyrazole, 2-hydroxypyridine, hydroquinone, resorcinol, catechol or alcohols such as C$_1$-C$_{20}$-alcohol, glycol, glycerol.

The present process can also be utilized advantageously as a dry process. Here, the protic compound water is removed from an aprotic solvent.

For the purposes of the present invention, aprotic solvents are, in particular, apart from the hydrocarbons defined further below:

chlorinated alkanes such as methylene chloride, chloroform or carbon tetrachloride;

aliphatic and alicyclic ethers such as diethyl ether, methyl tert-butyl ether or tetrahydrofuran;

ketones such as acetone, 2-butanone or 3-butanone;

carboxylic esters such as ethyl acetate, ethyl acetoacetate, butyl acetate or 2-ethylhexyl acetate and amides such as N-methylpyrrolidone, dimethylformamide, tetramethylurea or hexamethylphosphoramide.

For the purposes of the present invention, hydrocarbons can be aliphatic compounds such as alkanes. Preferred alkanes are branched or unbranched propane, butane, pentane, hexane, heptane, octane, nonane or decane or alkane mixtures which are customarily used as solvents and also cycloalkanes such as cyclopentane or cyclohexane. Various light petroleum fractions such as Solvesso® are possible here.

Olefins such as ethylene, propene, butene, butadienes, cyclohexadiene, cyclohexene, hexadiene, hexene or pentene are also suitable as hydrocarbon.

Further possible hydrocarbons are aromatic solvents such as benzene, toluene, o,m,p-xylene, mesitylene, cumene, pseudocumene, hemellitol, ethylbenzene, anisole, styrene, stilbene, tert-butylbenzene, dinitrobenzene, chlorobenzene, dichlorobenzene, nitrobenzene or benzonitrile. Particular preference is given to using toluene and in particular chlorobenzene.

It is also possible to use hydrocarbon mixtures composed of various alkanes, olefins, aromatics or else mixtures of alkanes and olefins, alkanes and aromatics or olefins and aromatics.

The following purities can advantageously be extracted according to the present invention from aliphatic hydrocarbons by means of ionic liquids: alcohols such as C$_1$-C$_{20}$-alkanols, polyols, geminal diols (hydrates); amines such as aniline, N—C$_1$-C$_{20}$-alkylaniline, N—C$_1$-C$_{20}$-alkylamine, N,N-di-C$_1$-C$_{20}$-alkylamine, cyclic amines such as piperidine, piperazine, pyrrolidine, morpholine and ammonium salts; phosphines; amidines; hydrazines and hydrazinium salts, hydrazones; hydroxylamines and hydroxylammonium salts; carbamates; ureas; imines such as imidazole, aldimines (Schiff bases), ketimines and iminium salts; hydroperoxides such as tert-butyl hydroperoxide; imides such as phthalimide; oximes; hydrogen peroxide; water ("drying of solvents"); phenols such as hydroquinones, resorcinols, catechols, naphthol, binaphthol; phosphinous acids; phosphinic acids; phosphonic acids; monoalkyl (or aryl) phosphonates; phosphoric acids; monoalkyl (or aryl) phosphates; dialkyl (or aryl) phosphates; carboxylic acids; amino acid; hydroxycarboxylic acids; ketocarboxylic acids; hydroxamic acids; hydroxamosulfonic acids; sulfinic acid; sulfonic acids or peroxycarboxylic acids.

The following impurities can particularly preferably be extracted from aliphatic hydrocarbons: alcohols, diols, polyols; amines; phosphines; imines; aldimines, ketimines; ureas; hydrazines; hydroperoxides; hydroxylamines; imides; oximes; phenols, hydroquinones, resorcinols, catechols, naphthol, binaphthol; peroxycarboxylic acids; carboxylic acids; amino acids; phosphinous acids, phosphinic acids, phosphonic acids, monoalkyl (or aryl) phosphonates, sulfinic acids, sulfonic acids.

In particular, the following protic compounds can be extracted from aromatic hydrocarbons using the process of the present invention:

alcohols such as $C_1$-$C_{20}$-alkanols, polyols; amines such as aniline, N—$C_1$-$C_{20}$-alkylaniline, N—$C_1$-$C_{20}$-alkylamine, N,N-Di-$C_1$-$C_{20}$-alkylamine, cyclic amines such as piperidine, piperazine, pyrrolidine, morpholine and ammonium salts; phosphines; amidines; hydrazines and hydrazinium salts, hydrazones; hydroxylamines and hydroxylammonium salts; carbamates; ureas; imines such as imidazole, aldimines (Schiff bases), ketimines and iminium salts; hydroperoxides such as tert-butyl hydroperoxide; imides such as phthalimide; oximes; hydrogen peroxide; water ("drying of solvents"); phenols such as hydroquinones, resorcinols, catechols, naphthol, binaphthol; phosphinous acids; phosphinic acids; phosphonic acids; monoalkyl (or aryl) phosphonates; phosphoric acids; monoalkyl (or aryl) phosphates; dialkyl (or aryl) phosphates; carboxylic acids; amino acids; hydroxycarboxylic acids; ketocarboxylic acids; hydroxamic acids; hydroxamosulfonic acids; sulfinic acids; sulfonic acids or peroxycarboxylic acids.

Particular preference is given to extracting the following impurities from aromatic hydrocarbons: alcohols, diols, polyols; amines; phosphines; imines; aldimines, ketimines; ureas; carbamates, hydrazines; hydroperoxides; hydroxylamines; imides; oximes; phenols, hydroquinones, resorcinols, catechols, naphthol, binaphthol; peroxycarboxylic acids; carboxylic acids; amino acids; phosphinous acids; phosphinic acids, phosphonic acids, monoalkyl (or aryl) phosphonates, sulfinic acids, sulfonic acids.

In the definitions of the symbols in the above formulae, use was made of collective terms which are generally representative of the following substitutents:

Halogen: fluorine, chlorine, bromine and iodine;

Alkyl: saturated, straight-chain or branched hydrocarbon radicals having from 1 to 4 or 6, 12, 20 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having from 1 to 12 carbon atoms (as mentioned above) in which the hydrogen atoms can be partly or completely replaced by halogen atoms as mentioned above, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

five- to six-membered saturated, partially unsaturated or aromatic heterocycle comprising from one to four heteroatoms from the group consisting of O, N and S:

5- or 6-membered heterocyclyl comprising from one to three nitrogen atoms and/or an oxygen or sulfur atom or one or two oxygen and/or sulfur atoms, e.g. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

5-membered heteroaryl comprising from one to four nitrogen atoms or from one to three nitrogen atoms and a sulfur or oxygen atom: 5-membered heteroaryl groups which can comprise from one to four nitrogen atoms or from one to three nitrogen atoms and a sulfur or oxygen atom as ring members in addition to carbon atoms, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl comprising from one to three or from one to four nitrogen atoms: 6-membered heteroaryl groups which can comprise from one to three or from one to four nitrogen atoms as ring members in addition to carbon atoms, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The ionic liquid is generally selected so that it has a miscibility of less than 10%, preferably less than 5%, with the hydrocarbon at room temperature. Suitable ionic liquids are generally those which form two separate phases with the hydrocarbon.

In general, the process of the present invention is able to reduce the contamination by at least 5%, frequently by more than 50% and preferably by more than 90%, in one extraction step. The extraction process can usually be carried out in one or more stages, batchwise or continuously. If desired, the extraction process is carried out under an inert gas atmosphere (nitrogen, noble gases, carbon dioxide).

Usual extraction times range from less than one minute to 2 hours. Preference is given to contact times of the two phases of less than one hour.

Depending on the melting point of the ionic liquid, temperatures of less than/equal to 100° C. are set. Typical extraction temperatures are from 10 to 100° C., preferably from 25 to 80° C.

The extraction can be carried out under atmospheric pressure or under a pressure of up to 200 atm.

Usual extraction apparatuses are mixer-settler systems, columns of various constructions, e.g. tray columns, bubble columns, columns containing ordered or random packing, rotating disk columns and vibratory plate columns, and plate separators.

After the extraction is complete, phase separation can be carried out by methods known from the literature.

Recirculation of the Ionic Liquid

Ionic liquids have a low vapor pressure and are very thermally stable. The ionic liquids are preferably recirculated by separating off the impurity by distillation or reextraction.

The removal of the impurity by distillation is preferably carried out in a thin film evaporator. The reextraction can be carried out using, in particular, media which likewise have a miscibility gap with the ionic liquid. Suitable media for reextraction are, for example, polar hydrocarbons such as halogenated hydrocarbons, supercritical carbon dioxide, ketones, esters, nitriles, ureas, ethers, polyethers and polyols.

The way in which the process functions will be illustrated below by means of an example. The separation problem on which this is based is as follows. The cleavage of kresoxim methyl in the presence of iron(III) chloride in chlorobenzene forms not only the desired 2-chloromethylphenylacetic α-O-methyloxime (CIMO) but also equimolar amounts of o-cresol.

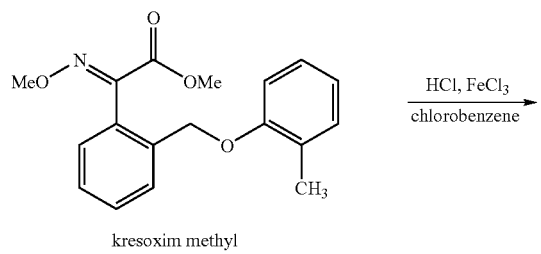

kresoxim methyl

CLMO          o-cresol

In the conventional removal of cresol by means of alkalis such as dilute aqueous sodium hydroxide, the CIMO which is sensitive under alkaline conditions is partly decomposed.

A test has therefore been carried out to determine whether extraction by means of acidic ionic liquids is possible. CIMO is stable in a nonaqueous, acidic medium. The following experiment shows that the acidic ionic liquid 1-ethyl-3-methylimidazolium hydrogen sulfate (EMIM HSO$_4$) as extractant displays excellent selectivities in respect of o-cresol. Even after a single extraction, o-cresol can be completely removed according to HPLC. The recovery of CIMO after extraction is 98%.

EXAMPLE 1

Extraction of O-cresol from Chlorobenzene by Means of EMIM HSO$_4$

The extraction was carried out at 80° C. in order to reduce the viscosity of the ionic liquid. The extraction time was in each case 15 minutes. To achieve optimal separation of the phases, centrifugation was carried out before separation. The phase boundary could be recognized very readily, and the separation of the phases was complete. The EMIM HSO$_4$ used for the extraction was presaturated with the solvent (chlorobenzene).

| Medium | Amount g | % by weight of o-cresol | g of o-cresol | Total g of trans/cis-oxime |
|---|---|---|---|---|
| Ionic liquid added | 80 | 0 | 0 | 0 |
| Org. phase starting material | 80 | 2.11 | 1.688 | 4.312 |
| Upper phase after 1st washing | 72.5 | 0 | 0 | 4.176 |
| Lower phase after 1st washing | 81.8 | 1.75 | 1.4315 | 0.01636 |
| Upper phase used in 2nd extraction | 69 | 0 | 0 | 3.9744 |
| Upper phase after 2nd washing | 64 | 0 | 0 | 3.7184 |
| Lower phase after 2nd washing | 73.5 | 0 | 0 | 0 |

Mass balance:

| | |
|---|---|
| Used in 1st extraction: | 160.0 g (total) |
| Obtained after 1st extraction: | 154.3 g |
| Losses (evaporation, flask): | 5.7 g (3.6%) |
| Used in 1st extraction: | 80.0 g (upper phase) |
| Obtained after 1st extraction: | 72.5 g |
| Obtained after 1st extraction (theoretical): | 78.4 g |
| Losses (evaporation, flask): | 1.6 g (2.0%) |
| Used in 2nd extraction: | 146.5 g (total) |
| Obtained after 2nd extraction: | 137.5 g |
| Losses (evaporation, flask): | 9.0 g (6.1%) |
| Used in 2nd extraction: | 69.0 g (upper phase) |
| Obtained after 2nd extraction: | 64.0 g |
| Obtained after 2nd extraction (theoretical): | 68.9 g |
| Losses (evaporation, flask): | 4.9 g (7.1%) | o-Cresol can, according to HPLC, be removed completely from the organic phase by means of one extraction step. More precise analysis by GC showed that the concentration of o-cresol can be reduced to <50 ppm after two extractions. CLMO is stable toward the ionic liquid even at 80° C.

EXAMPLE 2

Removal of Water from Aprotic Solvents a) Bismethylimidazolium Sulfate (MMIM $SO_4$):
   8.61 g (0.12 mol) of THF were mixed with 4.81 g (0.27 mol) of water. The water content of the solution was determined by the Karl-Fischer method (36%). 4.24 g (0.014 mol) of bismethylimidazolium sulfate were added to the solution. The two-phase solution was stirred for 15 min. The water content of the upper phase was determined (3.5%). Another 6.11 g (0.02 mol) of bismethylimidazolium sulfate were then added to the reaction mixture, the mixture was stirred for 15 min and the phases were separated. The water content of the upper phase was determined (1.2%). 0.07 g (0.004 mol) of water was present in the organic phase. 1 equivalent of bismethylimidazolium sulfate has therefore taken up 78 equivalents of water. The water could be removed completely (water content<0.1%) from the ionic liquid under reduced pressure (3 mbar).

b) Bismethylimidazolium Sulfate (MMIM $SO_4$):
   7.86 g (0.13 mol) of acetone were mixed with 4.93 g (0.27 mol) of water. The water content of the solution was determined by the Karl-Fischer method (39%). 5.03 g (0.017 mol) of bismethylimidazolium sulfate were added to the solution. The two-phase solution was stirred for 15 min. The water content of the upper phase was determined (6.85%). Another 5.82 g (0.02 mol) of bismethyl-imidazolium sulfate were then added to the reaction mixture, the mixture was stirred for 15 min and the phases were then separated. The water content of the upper phase was determined (2.3%). This corresponded to 0.12 g (0.006 mol) of water in the organic phase. A total of 0.264 mol of water was removed by 0.037 mol of bismethylimidazolium sulfate. The water could be removed completely (water content<0.1%) from the ionic liquid under reduced pressure (3 mbar).

c) Bismethylimidazolium Sulfate (MMIM $SO_4$):
   17.58 g (0.24 mol) of THF were mixed with 1.95 g (0.1 mol) of water. The water content of the solution was determined by the Karl-Fischer method (10.4%). 5.31 g (0.018 mol) of bismethylimidazolium sulfate were added to the solution. The two-phase solution was stirred for 15 min. The water content of the upper phase was determined (0.7%). This corresponded to 0.11 g (0.006 mol) of water in the organic phase. A total of 0.094 mol of water was removed by 0.018 mol of bismethylimidazolium sulfate. The water could be removed completely (water content<0.1%) from the ionic liquid under reduced pressure (3 mbar).

d) Bismethylimidazolium Sulfate (MMIM $SO_4$):
   15.5 g (0.26 mol) of acetone were mixed with 1.87 g (0.1 mol) of water. The water content of the solution was determined by the Karl-Fischer method (11.1%). 5.6 g (0.017 mol) of bismethylimidazolium sulfate were added to the solution. The two-phase solution was stirred for 15 min. The water content of the upper phase was determined (1.4%). This corresponded to 0.2 g (0.01 mol) of water in the organic phase. A total of 0.09 mol of water was removed by 0.017 mol of bismethylimidazolium sulfate. The water could be removed completely (water content<0.1%) from the ionic liquid under reduced pressure (3 mbar).

e) Bisbutylmethylimidazolium Sulfate (BMIM $SO_4$):
   87.78 g (1.2 mol) of THF were mixed with 19.67 g (1.1 mol) of water. The water content of the solution was determined by the Karl-Fischer method (19%). 44.35 g (0.12 mol) of bisbutylmethylimidazolium sulfate were added to the solution. The two-phase solution was stirred for 15 min. The water content of the upper phase was determined (1.9%). This corresponded to 1.54 g (0.08 mol) of water in the organic phase. A total of 1.02 mol of water was removed by 0.12 mol of bisbutylmethylimidazolium sulfate. The water could be removed completely (water content<0.1%) from the ionic liquid under reduced pressure (3 mbar).

f) Bisbutylmethylimidazolium Sulfate (BMIM $SO_4$):
   77.42 g (1.33 mol) of acetone were mixed with 19.94 g (1.1 mol) of water. The water content of the solution was determined by the Karl-Fischer method (20.8%). 48.26 g (0.13 mol) of bisbutylmethylimidazolium sulfate were added to the solution. The two-phase solution was stirred for 15 min. The water content of the upper phase was determined (3.3%). This corresponded to 2.2 g (0.12 mol) of water in the organic phase. A total of 0.98 mol of water was removed by 0.13 mol of bisbutylmethylimidazolium sulfate. The water could be removed completely (water content<0.1%) from the ionic liquid under reduced pressure (3 mbar).

g) Bisbutylethylimidazolium Sulfate (BEIM $SO_4$):
   87.52 g (1.2 mol) of THF were mixed with 21.45 g (1.1 mol) of water. The water content of the solution was determined by the Karl-Fischer method (20%). 49.2 g (0.12 mol) of bisbutylethylimidazolium sulfate were added to the solution. The two-phase solution was stirred for 15 min. The water content of the upper phase was determined (2.1%). This corresponded to 1.62 g (0.09 mol) of water in the organic phase. A total of 1.01 mol of water was removed by 0.12 mol of bisbutylmethylimidazolium sulfate. The water could be removed completely (water content<0.1%) from the ionic liquid under reduced pressure (3 mbar).

h) Bismethylimidazolium Sulfate (MMIM $SO_4$):
   8.61 g (0.12 mol) of THF were mixed with 4.81 g (0.27 mol) of water. The water content of the solution was determined by the Karl-Fischer method (36%). 4.24 g (0.014 mol) of bismethylimidazolium sulfate were added to the solution. The two-phase solution was stirred for 15 min. The water content of the upper phase was determined (3.5%). Another 6.11 g (0.02 mol) of bismethylimidazolium sulfate were then added to the reaction mixture, the mixture was stirred for 15 min and the phases were then separated. The water content of the upper phase was determined (1.2%). This corresponded to 0.07 g (0.004 mol) of water in the organic phase. A total of 0.266 mol of water was removed by 0.034 mol of bismethylimidazolium sulfate. The water could be removed completely (water content<0.1%) from the ionic liquid under reduced pressure (3 mbar).

i) Bismethylimidazolium Sulfate (MMIM $SO_4$):
   7.86 g (0.13 mol) of acetone were mixed with 4.93 g (0.27 mol) of water. The water content of the solution was determined by the Karl-Fischer method (39%). 5.03 g (0.017 mol) of bismethylimidazolium sulfate were added to the solution. The two-phase solution was stirred for 15 min. The water content of the upper phase was determined (6.85%). Another 5.82 g (0.02 mol) of bismethyl-imidazolium sulfate were then added to the reaction mixture, the mixture was stirred for 15 min and the phases were then separated. The water content of the upper phase was determined (2.3%). This corresponded to 0.12 g (0.006 mol) of water in the organic phase. A total of 0.264 mol of water was removed by 0.037 mol of bismethylimidazolium sulfate. The water could be removed completely (water content<0.1%) from the ionic liquid under reduced pressure (3 mbar).

j) Bismethylimidazolium Sulfate (MMIM $SO_4$):

17.58 g (0.24 mol) of THF were mixed with 1.95 g (0.1 mol) of water. The water content of the solution was determined by the Karl-Fischer method (10.4%). 5.31 g (0.018 mol) of bismethylimidazolium sulfate were added to the solution. The two-phase solution was stirred for 15 min. The water content of the upper phase was determined (0.7%). This corresponded to 0.11 g (0.006 mol) of water in the organic phase. A total of 0.094 mol of water was removed by 0.018 mol of bismethylimidazolium sulfate. The water could be removed completely (water content<0.1%) from the ionic liquid under reduced pressure (3 mbar).

k) Bismethylimidazolium Sulfate (MMIM $SO_4$):

15.5 g (0.26 mol) of acetone were mixed with 1.87 g (0.1 mol) of water. The water content of the solution was determined by the Karl-Fischer method (11.1%). 5.6 g (0.017 mol) of bismethylimidazolium sulfate were added to the solution. The two-phase solution was stirred for 15 min. The water content of the upper phase was determined (1.4%). This corresponded to 0.2 g (0.01 mol) of water in the organic phase. A total of 0.09 mol of water was removed by 0.017 mol of bismethylimidazolium sulfate. The water could be removed completely (water content<0.1%) from the ionic liquid under reduced pressure (3 mbar).

l) Bisbutylmethylimidazolium Sulfate (BMIM $SO_4$):

87.78 g (1.2 mol) of THF were mixed with 19.67 g (1.1 mol) of water. The water content of the solution was determined by the Karl-Fischer method (19%). 44.35 g (0.12 mol) of bisbutylmethylimidazolium sulfate were added to the solution. The two-phase solution was stirred for 15 min. The water content of the upper phase was determined (1.9%). This corresponded to 1.54 g (0.08 mol) of water in the organic phase. A total of 1.02 mol of water was removed by 0.12 mol of bisbutylmethylimidazolium sulfate. The water could be removed completely (water content<0.1%) from the ionic liquid under reduced pressure (3 mbar).

m) Bisbutylmethylimidazolium Sulfate (BMIM $SO_4$):

77.42 g (1.33 mol) of acetone were mixed with 19.94 g (1.1 mol) of water. The water content of the solution was determined by the Karl-Fischer method (20.8%). 48.26 g (0.13 mol) of bisbutylmethylimidazolium sulfate were added to the solution. The two-phase solution was stirred for 15 min. The water content of the upper phase was determined (3.3%). This corresponded to 2.2 g (0.12 mol) of water in the organic phase. A total of 0.98 mol of water was removed by 0.13 mol of bisbutylmethylimidazolium sulfate. The water could be removed completely (water content<0.1%) from the ionic liquid under reduced pressure (3 mbar).

n) Bisbutylethylimidazolium Sulfate (BEIM $SO_4$):

87.52 g (1.2 mol) of THF were mixed with 21.45 g (1.1 mol) of water. The water content of the solution was determined by the Karl-Fischer method (20%). 49.2 g (0.12 mol) of bisbutylethylimidazolium sulfate were added to the solution. The two-phase solution was stirred for 15 min. The water content of the upper phase was determined (2.1%). This corresponded to 1.62 g (0.09 mol) of water in the organic phase. A total of 1.01 mol of water was removed by 0.12 mol of bisbutylmethylimidazolium sulfate. The water could be removed completely (water content<0.1%) from the ionic liquid under reduced pressure (3 mbar).

We claim:

1. A process for the extractive removal of optionally substituted phenol, 3-hydroxypyrazole, 2-hydroxypyridine, hydroquinone, resorcinol, catechol; $C_1$-$C_{20}$-alcohol, glycol, glycerol, optionally substituted aniline, N—$C_1$-$C_{20}$-alkylamine, N,N-di-$C_1$-$C_{20}$-alkylamine, P—$C_1$-$C_{20}$-alkylphosphine, P,P-di-$C_1$-$C_{20}$-alkylphosphine, phenylphosphine, diphenylphosphine, hydrazine, hydroxylamine, sulfonic acid, sulfinic acid, phosphoric acid, carboxylic acid or amino acid from aprotic solvents by means of ionic liquids of the formula $[K]_n^+[A]^{n-}$, where n is 1, 2 or 3;

[K]+ is selected from the group consisting of:

quaternary ammonium cations of the formula $[NR^1, R^2, R^3, R^4]^+$ (Ia), quaternary phosphonium cations of the formula $[PR^1, R^2, R^3, R^4]^+$ (Ib), where $R^1$, $R^2$, $R^3$, $R^4$ are each $C_1$-$C_{12}$-alkyl or phenyl-$C_1$-$C_4$-alkyl, where the aliphatic radicals may bear from 1 to 4 substituents selected from the group consisting of halogen, amino, cyano, $C_1$-$C_4$-alkoxy and the phenyl ring may bear the abovementioned substitutents and also $C_1$-$C_6$-alkyl, carboxylate and sulfonate groups;

$R^1$ and $R^2$ may together form a $C_4$-$C_5$-alkenylene radical which may be substituted by $C_1$-$C_4$-alkyl, halogen, cyano or $C_1$-$C_4$-alkoxy;

imidazolium cations of the formula,

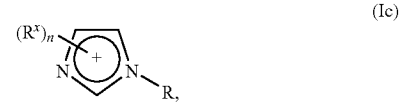

(Ic)

pyridinium cations of the formula,

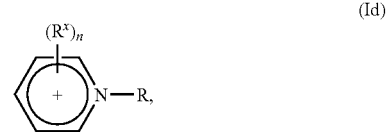

(Id)

pyrazolium cations of the formula,

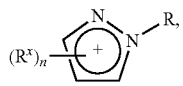
(Ie)

quinolinium cations of the formula,

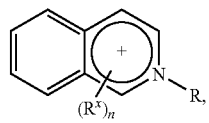
(If)

thiazolium cations of the formula,

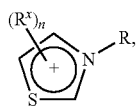
(Ig)

triazinium cations of the formula,

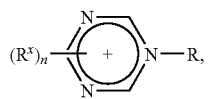
(Ih)

where the index n and the substitutents R and $R^x$ have the following meanings:

n is 0, 1, 2, 3 or 4;

R is hydrogen, $C_1$-$C_{12}$-alkyl or phenyl-$C_1$-$C_4$-alkyl, where the aliphatic radicals may bear from 1 to 4 substitutents selected from the group consisting of halogen, amino, cyano, $C_1$-$C_4$-alkoxy and the phenyl ring may bear the abovementioned substitutents and also $C_1$-$C_6$-alkyl, carboxylate and sulfonate groups;

$R^x$ is $C_1$-$C_6$-alkyl, halogen, amino, cyano, $C_1$-$C_4$-alkoxy, carboxylate or sulfonate;

$[A]^{n-}$ is the partly or fully deprotonated anion of an inorganic or organic protic acid $H_nA$ (III), where n is a positive integer and indicates the charge on the anion.

2. The process according to claim 1, wherein the organic compound to be extracted is a phenol or alcohol.

3. The process according to claim 1, wherein the aprotic solvent is a hydrocarbon.

4. The process according to claim 1, wherein the hydrocarbon is an alkane or halogenated alkane.

5. The process according to claim 1, wherein the hydrocarbon is an arene which is optionally substituted by halogen, nitro, cyano, $C_1$-$C_3$-alkyl, $C_1$-$C_3$-alkoxy or methoxycarbonyl.

6. The process according to claim 1, wherein the ionic liquid is an ammonium or imidazolium salt or a mixture of these salts.

7. The process according to claim 1, wherein the ionic liquid is a sulfate or hydrogensulfate.

8. The process according to claim 1, wherein a phenol is removed from chlorobenzene.

9. The process according to claim 1, wherein the extracted impurity is separated off from the ionic liquid by distillation.

10. The process according to claim 1, wherein the extracted impurity is separated off from the ionic liquid by reextraction.

11. The process according to claim 2, wherein the aprotic solvent is a hydrocarbon.

12. The process according to claim 2, wherein the hydrocarbon is an alkane or halogenated alkane.

13. The process according to claim 3, wherein the hydrocarbon is an alkane or halogenated alkane.

14. The process according to claim 2, wherein the hydrocarbon is an arene which is optionally substituted by halogen, nitro, cyano, $C_1$-$C_3$-alkyl, $C_1$-$C_3$-alkoxy or methoxycarbonyl.

15. The process according to claim 3, wherein the hydrocarbon is an arene which is optionally substituted by halogen, nitro, cyano, $C_1$-$C_3$-alkyl, $C_1$-$C_3$-alkoxy or methoxycarbonyl.

16. The process according to claim 2, wherein the ionic liquid is an ammonium or imidazolium salt or a mixture of these salts.

17. The process according to claim 3, wherein the ionic liquid is an ammonium or imidazolium salt or mixture of these salts.

18. The process according to claim 4, wherein the ionic liquid is an ammonium or imidazolium salt or a mixture of these salts.

19. The process according to claim 5, wherein the ionic liquid is an ammonium or imidazolium salt or a mixture of these salts.

20. The process according to claim 2, wherein the ionic liquid is a sulfate or hydrogensulfate.

* * * * *